(12) United States Patent
Samsoondar et al.

(10) Patent No.: US 7,198,955 B1
(45) Date of Patent: Apr. 3, 2007

(54) METHOD AND APPARATUS FOR MEASUREMENT OF BLOOD SUBSTITUTES

(75) Inventors: James Samsoondar, Cambridge (CA); Duncan MacIntyre, Campbellville (CA)

(73) Assignee: NIR Diagnostics Inc., Waterloo, Ontario (CA)

(*) Notice: Subject to any disclaimer, the term of this patent is extended or adjusted under 35 U.S.C. 154(b) by 0 days.

(21) Appl. No.: 09/367,859

(22) PCT Filed: Oct. 16, 1997

(86) PCT No.: PCT/CA97/00759

§ 371 (c)(1),
(2), (4) Date: Sep. 2, 1999

(87) PCT Pub. No.: WO98/39634

PCT Pub. Date: Sep. 11, 1998

Related U.S. Application Data (60) Provisional application No. 60/038,554, filed on Mar. 3, 1997.

(51) Int. Cl.
  G01N 33/72 (2006.01)
  G01N 33/20 (2006.01)
  G01N 33/62 (2006.01)
  G01N 33/68 (2006.01)
  G01N 33/48 (2006.01)
  C12Q 1/00 (2006.01)

(52) U.S. Cl. ............... 436/66; 356/39; 435/15; 435/17; 435/21; 435/26; 436/71; 436/73; 436/79; 436/86; 436/87; 436/88; 436/89; 436/90; 436/91; 436/92; 436/93; 436/94; 436/95; 436/96; 436/97; 436/98; 436/99; 436/100; 436/125; 436/164; 436/171; 436/175; 436/183

(58) Field of Classification Search .............. 436/66, 436/71, 73, 79, 86–100, 164, 171, 175, 183, 436/125; 356/39; 435/15, 17, 21, 26
See application file for complete search history.

(56) References Cited

U.S. PATENT DOCUMENTS 3,703,336 A * 11/1972 Rosse et al. ............... 356/39
4,043,756 A * 8/1977 Sommervold .............. 436/43
4,263,512 A * 4/1981 Sagusa et al. ............. 250/373
4,627,014 A * 12/1986 Lo et al. .................... 702/25
4,935,346 A * 6/1990 Phillips et al. ............ 435/14
5,057,435 A * 10/1991 Denney ..................... 436/79
5,416,026 A * 5/1995 Davis ........................ 436/66
5,841,523 A * 11/1998 Degen et al. .............. 356/72
5,846,492 A * 12/1998 Jacobs et al. .............. 422/67
6,207,459 B1 * 3/2001 Weisheit et al. ........... 436/66
6,268,910 B1 * 7/2001 Samsoondar et al. ...... 356/39

FOREIGN PATENT DOCUMENTS

EP  0 158 506 A  10/1985

EP  0 415 401 A  3/1991

OTHER PUBLICATIONS

B.F. Stimmel J. Biol. Chem. 1946, 165, 73-80.*
W. R. D. Golden et al, J. Lab. Clin. Med. 1948, 33, 890-903.*
L. H. Hamilton J. Lab. Clin. Med. 1958, 52, 762-767.*
H. A. Sloviter et al, Nature 1967, 216, 458-460.*
S. D. Simon et al, Transfusion 1982, 22, 341-342.*
R. E. Mullins et al, Am. J. Clin. Pathol. 1983, 80, 478-483.*
J. T. Lin et al. Anal. Chem. 1986, 58, 830-833.*
W. L. Fitch et al, Anal. Biochem. 1986, 154, 632-637.*
K. L. J. Vink et al, Clin. Chem. 1988, 34, 67-70.*
H. Chai et al, J. WCUMS 1989, 20, 223-225.*
R. F. Lacey Appl. Spectrosc. 1989, 43, 1135-1139.*
A. G. Randall et al, Ann. Clin. Biochem. 1990, 27, 345-352.*
R. H. Christenson et al, Clin. Chem. 1993, 39, 1129, abstract 0046.*
N. Leissing et al, Clin. Chem. 1993, 39, 1133, abstract 0115.*
D. W. Jay et al, Clin. Chem. 1993, 39, 1804-1810.*
M. C. Pascual-Marti et al, Fresenius J. Anal. Chem. 1993, 347, 305-313.*
E. A. Korany et al, Alexandria Eng J. 1996, 35, B63-B71.*
P. L. Lopez-de-Alba et al, Anal. Chim. Acta 1996, 330, 19-29.*
A. C. Y. Ali et al, Clin. Chem. 1997, 43, 1794-1796.*
R. G> Martinek J. Am. Med. Technologists 1966, 28, 42-58.*
M. Lubran Med. Clin. N. Amer. 1969, 53, 211-222.*
M. J. Milano et al, Anal. Chem. 1977, 49, 555-559.*
K. Amazon et al, Am. J. Clin. Pathol. 1981, 75, 519-523.*
M. Caselli et al, Anal. Lett. 1981, 14, 1465-1481.*
T. J. Siek et al, J. Forensic Sci. 1984, 29, 39-54.*
F. G. Soloni et al, Am. J. Clin. Pathol. 1986, 85, 342-347.*
M. F. Merrick et al, Clin. Chem. 1986, 32, 598-602.*
J. A. Gimpel et al, J. Clin. Chem. Clin. Biochem. 1989, 27, 217-219.*
B. E. Copelend et al, Ann. Clin. Lab. Sci. 1989, 19, 383-388.*
B. E. Copelend et al, Am. J. Clin. Pathol. 1989, 92, 619-624.*
K. Ikemura et al, Rinsho Byori 1990, 38, 87-92.*
J. M. Cawstro-Romero et al, Microchem. J. 1991, 43m 104-108.*
A. Espinosa-Mansilla ety al, Analyst 1993, 118, 89-95.*
F. Navarro-Villoslada et al, Anal. Chim. Acta 1995, 313, 93-101.*
R. D. Bautista et al, Fresenius' J. Anal. Chem. 1997, 357, 449-456.*
M. Blanco et al, Fresnius' J. Anal. Chem. 1995, 351, 315-319.*
Hanson, N. Q. et al, American Journal of Medical Technology 1973, 39, 299-305.*

(Continued)

Primary Examiner—Arlen Soderquist
(74) Attorney, Agent, or Firm—Schwegman, Lundberg, Woessner and Kluth P.A.

(57) ABSTRACT

A method is disclosed whereby the concentration of a blood substitute, such as cross-linked hemoglobin, in a serum or plasma specimen is rapidly and accurately identified and quantified. The method further takes the measured concentration of the blood substitute and uses it to correct for its effect, if any, on a measured analyte concentration, e.g., serum/plasma total protein. Further, the method allows for the determination of the concentration of true hemoglobin in the presence of blood substitutes. The method is carried out in respect of samples contained in a primary or secondary labelled tube, or a pipette tip used to dispense serum or plasma in a blood analyzer.

13 Claims, 7 Drawing Sheets

OTHER PUBLICATIONS

Hasson, W. et al, Clinical Chemistry 1974, 20, 15-18.*
Norris, K. A. et al, Clinical Chemistry 1975, 21, 1093-1101.*
Savory, J. et al, Clinical Chemistry 1976, 22, 1102-1104.*
Teppo, A. M., Clinical Chemistry 1982, 28, 1359-1361.*
DeGrella, R. F. et al, Clinical Chemistry 1985, 31, 1474-1477.*
Corns, C. M., Annals of Clinical Biochemistry 1987, 24, 591-597.*
Waymack, P. P. et al, Clinical Chemistry 1993, 39, 2058-2062.*
Mazzachi, R. D. et al, European Journal of Clinical Chemistry and Clinical Biochemistry 1994, 32, 709-715.*
Nielsen, N. C., Scandinavian Journal of Clinical and Laboratory Investigation 1963, 15, 613-621.*
Horak, E. et al, Annals of Clinical and Laboratory Science 1974, 4, 87-94.*
Manasterski, A. et al, Mikrochimica Acta 1975, 2, 1-16.*
Fritsche, H. A. et al, Clinical Biochemistry 1975, 8, 240-246.*
Boigne, J. M. et al, Annales de Biologie Clinique 1977, 35, 237-254.*
Perlstein, M. T. et al, Microchemical Journal 1977, 22, 403-419.*
Puukka, R. et al, Scandinavian Journal of Clinical and Laboratory Investigation 1978, 38, 189-192.*
Hubsch, G. et al, Journal of Clinical Chemistry and Clinical Biochemistry 1980, 18, 149-155.*
Soldin, S. J. et al, Clinical Biochemistry 1981, 14, 165-168.*
Painter, P. C. et al, Journal of Clinical Laboratory Automation 1981, 1, 113-119.*
Karlsen, R. L. et al, Scandinavian Journal of Clinical and Laboratory Investigation 1983, 43, 175-177.*
Margrey, M. et al, Annals of Clinical and Laboratory Science 1984, 14, 298-303.*
Grafmeyer, D. et al, Spectra Biologie 1993, 93, 33-42.*
Huebner, G. H. et al, Therapeutic Drug Monitoring 1996, 18, 620-623.*
Fremont, S. et al, Annales de Biologie Clinique 1996, 54, 309-320.*
Pratt, R.G. et al., Biomaterials, Artificial Cells and Immobilization Technology, vol. 20, No. 2-4, p. 921-924 (1992).

* cited by examiner

METHOD AND APPARATUS FOR MEASUREMENT OF BLOOD SUBSTITUTES

This application is the National Stage of International Application No. PCT/CA97/00759, filed Oct. 16, 1997, which claims the benefit of U.S. Provisional Application No. 60/038,554, filed Mar. 3, 1997.

FIELD OF INVENTION

This invention relates to spectrophotometry and the spectrophotometric analysis of serum or plasma used for blood testing. It also relates to the effects of blood substitutes and other interferents on blood test results. In particular, this invention relates to a method for measuring blood substitutes in serum or plasma, determining the effects of blood substitutes on blood test results, and combining the two to adjust or correct blood test results for the presence of blood substitutes.

BACKGROUND OF INVENTION

Clinical laboratory tests are routinely performed on the serum or plasma of whole blood. In a routine assay, red blood cells are separated from plasma by centrifugation, or red blood cells and various plasma proteins are separated from serum by clotting prior to centrifugation.

Haemoglobin (Hb), bilirubin (BR), biliverdin (BV) and light-scattering substances like lipid particles are typical substances which will interfere with, and affect spectrophotometric and other blood analytical measurements. Such substances are referred to as interferents. Elevated Hb in the blood, haemoglobinemia, can be due to disease states and as a result of specimen handling. Elevated bile pigments, namely BR and BV, can be due to disease states. Increased lipid particles in the blood, also known as hyperlipidemia or lipemia, can be due to disease states and dietary conditions. Lipemia is the major cause of turbidity in serum and plasma, and therefore the terms lipemia and turbidity are frequently used interchangeably.

Many tests conducted on plasma or serum samples employ a series of reactions which terminate after the generation of chromophores which facilitate detection by spectrophotometric measurements at one or two wavelengths. Measurement of interfering substances prior to conducting such tests is important in providing meaningful and accurate test results. In fact if a sample is sufficiently contaminated with interferents, tests are normally not conducted as the results will not be reliable.

Another set of potential interferents is blood substitutes. Blood substitutes are new products which are under development, for use instead of whole blood or red blood cells for transfusion. Blood transfusion is a life-saving process performed after severe blood loss during trauma or surgery. Some advantages of using a blood substitute instead of blood or red blood cells are as follows: 1. blood substitutes are expected to be universally compatible with all blood types, therefore cross-matching will not be necessary; 2. maximum storage time of blood is 42 days, whereas blood substitutes could have a much longer shelf-life; 3. purification a blood substitute may include heat treatment, which may eliminate the threat of hazardous viruses such as HIV. However, a challenge blood substitutes will pose to the clinical laboratory is managing the effects of blood substitutes on blood tests. Some blood substitutes will cause serum or plasma specimens to appear as whole blood or severely hemolyzed serum or plasma, hence the term pseudohemolysis may be used to describe such specimens. Hemolysis, the liberation of Hb from red blood cells into serum or plasma, may account for about 2 g/L, but blood substitutes can account for as much as 30 g/L of cross-linked Hb (CLHb), in a patient treated for severe blood loss. However, true hemolysis will not only make serum and plasma specimens appear red, but high concentrations of certain analytes inside red cells, e.g. potassium, will elevate the concentration of analytes in a serum or plasma specimen. Therefore, the effect of Hb-based blood substitutes on blood test results, is more predictable than the effect of true hemolysis.

Current methods used for detecting haemoglobinemia, bilirubinemia and lipemia or turbidity utilize visual inspection of the specimen with or without comparison to a coloured chart.

Most blood substitutes under development are made from human Hb, but another type of blood substitute has been reported which is a milky-white emulsion containing tiny beads of perfluorocarbons wrapped in a surfactant. For example, such perfluorocarbons are described in R. G. Pratt et al. "Quantitation of perfluorocarbon blood substitutes in tissues using F-19 magnetic resonance spectroscopy" Biomaterials, Artificial Cells and Immobilization Technology, Vol. 20, No. 2–4, 1992, pages 921–924, XP002057067.

The former will create pseudohemolysis while the latter will create pseudolipemia, in serum and plasma specimens. Subunits of Hb-based blood substitute are chemically cross-linked for stability (CLHb) and produce absorbance spectra which are very similar to the absorbance spectra of normal hemoglobin (Hb). A method and apparatus for determining, by absorption spectrophotometry, an analyte, such as bilirubin or hemoglobin, in human serum, in the presence of unknown interferents is described in European Patent Application 0 158 506. However, the method relies upon wet chemistry and dry chemistry assays in order to make the analyte determinations.

As such, currently there is no method for rapidly adjusting blood test results which are effected by blood substitutes. The present invention describes such a method. The method and apparatus of the present invention for measuring the concentration of blood substitutes in the presence of Hb, BR, BV and turbidity: The results of measurements of blood substitutes obtained are used to correct blood test results affected by the blood substitutes. Further the levels of other interferents can be measured in the presence of the blood substitutes. Therefore, true hemolysis can be measured in the presence of blood substitutes which cause "pseudohemolysis".

SUMMARY OF THE INVENTION

According to one aspect of the present invention there is provided a method whereby the concentration of a blood substitute in a serum or plasma specimen is rapidly and accurately assessed, and the measured concentration is used to correct for its effect, if any, on a measured analyte concentration, e.g., serum/plasma total protein. There is no known prior art which can measure this interferent in a primary or secondary labelled tube, or a pipette tip used to dispense serum or plasma in a blood analyzer.

According to a further aspect of the present invention, spectral data is used in a novel way to determine if a specimen contains a blood substitute and if so, to what extent, in the presence and absence of other interferents.

According to another aspect of the present invention, other interferents, for example Hb, BR, BV and turbidity, can be accurately measured in the presence of blood substitutes.

According to still another aspect of the present invention, linear regression equations may be developed for different analytes in different blood analyzers by which it is possible to relate the measured concentration of an analyte to the amount of blood substitute present. The analyzers examined are the Kodak Ektachem 700 from Johnson and Johnson and the Hitachi 717 from Boehringer Mannheim; the former represents slide technology or the so-called dry chemistry (i.e., the only liquid involved in the test is the specimen being tested), and the latter represents the so-called wet chemistry. The blood substitute tested was CLHb from Hemosol Inc.

According to yet another aspect of the present invention, algorithms are developed which are analyte-specific and analyzer-specific, which can measure the amount of blood substitute present in the serum or plasma specimen, and make the necessary adjustment or correction to the measured analyte concentration, thereby removing the effect of the blood substitute.

Other advantages and novel features of the invention will become more apparent from the following detailed description when taken in conjunction with the accompanying drawings.

Definitions

Abbreviations as used herein have the following meaning:

| | |
|---|---|
| Na = | sodium |
| K = | potassium |
| Cl = | chlorine |
| $HCO_3$ = | bicarbonate |
| Ca = | calcium |
| Mg = | magnesium |
| GGT = | gamma glutamyl transfurase |
| AST = | aspartate amino transfurase |
| LDH = | lactate dehydrogenase |
| CK = | creatine kinase |
| ALP = | alkaline phosphatase |
| Tbili = | total bilirubin |

DETAILED DESCRIPTION OF THE INVENTION

The apparatus used in the present invention generally comprises a dual-beam-in-time spectrophotometer optically coupled to, or communicating with a sample holder through optical fibres. The sample can be a serum or plasma specimen in a labelled tube made of glass or plastic material or a plastic pipette tip used for dispensing the specimen in the blood analyzer. A robotic arm can be used to introduce the sample into the sample holder. It is understood that other conveyor transport mechanisms could be employed. Furthermore, any means by which the input and output fibre optic bundles are brought into alignment for measurement of absorption or reflectance in a specimen container is within the scope of the present invention. Along the side of the sample holder is a separate fibre for transmitting the reference light, when the shutter at the sample channel is closed and the shutter at the reference channel is open. Sample and reference dark scans can be performed with the sample in place with the sample holder closed, and both shutters closed, using the integration times used for the respective sample and reference light scans. There are no other shutters in the apparatus besides the sample path and reference path shutters. The spectrophotometer uses a fixed integration time for the reference beam and a choice of integration time for the sample beam.

Preferably the light source is a quartz-tungsten-halogen 10 watt lamp, but other wattage lamps can be employed. The input power supply is alternating current, but the output to the light source is a stabilized direct current. The spectral output from the light source is broad band covering the visible and NIR regions. The beam of radiation from light source is directed through a band-pass filter in the lamp assembly, and a shaping filter in the spectrophotometer. The band-pass filter is required to reduce unwanted radiation outside of 475–910 nm, and the shaping filter is required to "flatten" the detection system's optical response. The 475–910 nm wavelength range is used because this range can be used to measure the blood substitutes as well as other interferents, i.e., Hb, BR, BV and turbidity. A bifurcated bundle emerges from a main fibre connected to the output ligh source which provides random sampling of the lamp radiation to supply the sample and reference beams via two arms. The sample and reference beams reconverge at the spectrophotometer via the two arms of another bifurcated fibre bundle. In order to provide balanced emerging radiation to the linear photodiode array (PDA) detector, from both the sample and reference paths, 99% and 1% of the radiation from the main fibre must be directed through the sample and reference paths, respectively.

If the sample holder is not light-tight, i.e., capable of excluding external light, sample and reference dark scans have to be subtracted from the sample and reference light scans, respectively. If the sample holder is sufficiently light-tight, which is determined empirically, dark scans are omitted. Also, multiple scans can be averaged to minimize noise, but for the sake of speed single scans are used.

When in use, each pixel or wavelength portion is measured at the photodiode array approximately simultaneously during a particular scan. The optical radiation falling on each sensor element is integrated for a specified time and the individual pixels or wavelengths are sampled sequentially by a 16 bit analog-to-digital convertor or ADC.

Although the present embodiment details use of a PDA, any alternative means which provides a similar result is understood to be within the scope of the present invention.

For example a filter-wheel system may be used. In carrying out measurements each analyte uses from one to four wavelengths or pixels. Given that the first derivative of absorbance with respect to measurements with the PDA is the difference between the absorbance at two adjacent pixels, the first derivative of absorbance at one wavelength with a filter-wheel system will require the absorbance measured with two different narrow band-pass filters. It will be readily understood by those skilled in the art that the filters do not need to be assembled on a rotating wheel, but that any structure which achieves the result of a narrow band-pass filtration of absorbed radiation is within the scope of the present invention.

Another embodiment uses reflectance where the incident light is reflected off some reflective surface placed behind the sample.

Transmission is preferred over reflectance because the effect of the variation in absorbance due to the container in which the serum or plasma specimens reside, are insignificant for the wavelengths chosen. The variation in apparent absorbance due to markings on the labels can be handled effectively by using the first derivative of the apparent absorbance. The term "apparent" absorbance is used because when the amount of light transmitted through the sample is measured, and the transmitted light is converted to absorbance units, as discussed in the next paragraph; light attenuation by any means other than that which is absorbed by the sample will be interpreted as absorbance. For example, lipid particles will scatter light away from the detector, and the scattered light will be interpreted as absorbance. It is understood that determination of the concentration of interferents using reflectance is within the scope of this invention.

The PDA integrates the optical radiation over a specified time and converts the optical signal to a time multiplexed analog electronic signal called a scan where absorbance is calculated as:

where
- Absorbance$_i$ = log{(Reference Light$_i$ − Reference Dark$_i$)/(Sample Light$_i$ − Sample Dark$_i$)} + log (ITS/ITR)
- Absorbance$_i$ = Absorbance pixel i
- Reference Light$_i$ = Reference pixel i readings, with reference path open and sample path closed by a shutter;
- Reference Dark$_i$ = Reference pixel i readings, with reference and sample paths closed by shutters;
- Sample Light$_i$ = Sample pixel i readings, with sample path open and reference path closed by a shutter;
- Sample Dark$_i$ = Sample pixel i readings, with sample and reference paths closed by shutters;
- ITS = Integration time for sample measurement;
- ITR = Integration time for reference measurement; and
- i = the particular pixel (wavelength) in the PDA.

Depending on the required analyzer through-put and if the sample holder is sufficiently light-tight, dark scans are not necessary. The electronic signal is proportional to the time that the detector integrates the optical signal. The electronic signal is amplified by analog electronic amplifiers and converted to a digital signal by an analog-to-digital converter or ADC. The digital information from the converter is interpreted for data analysis by a microprocessor which is in turn connected via an RS232 connector to a computer. The results of the data analysis can be displayed on the computer, or on a printer connected to the computer. A user can control the device through the computer, to specify a particular interferent to be analyzed and to determine the number and timing of measurements.

Although a rapid pre-screening device could take as much time as one to two minutes per sample measurement and still be considered rapid in this field of art, the present invention allows for rapid pre-screening of samples by taking successive sample measurements at intervals of 5 seconds for 4 interferents and the blood substitute; for pipette tips and if no dark scan measurements are made with same tips, the spectral measurements can be made in up to one second. After the sample holder is opened, the sample is placed according to the controlling process and a sensor in the sample holder can activate the collection of spectral data.

The integration time for the sample beam is low for clear samples since there is less scattered light and therefore more light is transmitted to the detector. When the light is sufficiently scattered by, for example a turbid sample, the spectrophotometer will automatically switch to a higher integration time. Due to the linear relationship between the detector response and the IT, the second IT can be determined from the detector response of the low IT (or first IT). The higher integration time chosen will be within a pre-selected range such that the detector's response is optimal and within the linear-response range. This feature will allow all samples, from the clearest to the most turbid, to be efficiently screened without exceeding the linear response range of the detector.

As with any quantitative method, calibration of the spectrophotometer is required. However the method for NIR calibration is much more complex than most which can be calibrated with a minimum of a single standard material of known concentration. In respect of NIR calibration, samples must contain all interferents expected during the analysis of an unknown sample; the sample must contain an even distribution of the interferent of interest, and the concentrations of any two interferents should not correlate significantly. It is understood, that for any pre-screening, according to the present invention, of a typical sample for subsequent analysis, any combination of interferents may be present. The pre-screen allows for the determination of the concentration of any one in the presence or absence of the others. Although the data presented is based upon a particular blood substitute made by chemically cross linking the Hb subunits, it is understood that similar calibration algorithms for measuring other blood substitutes and correcting for their effects on blood test results, are within the scope of this invention. It is also understood that not only does "other blood substitutes" include those which are Hb-based, but any other blood substitute, e.g., those which appear as milky-white emulsion.

The first part of the process for generating a calibration curve is to store spectral data for the calibration set. The calibration algorithm for each interferent must be installed in a microprocessor so that when an unknown sample is tested for a particular interferent the result is produced quickly. In order to calculate the quantity of any interferent present, any one of several different methods, all of which are within the scope of this invention, may be used.

One approach would be to process the raw absorbance by multiple linear regression and choose wavelengths using standard procedures and statistics to find optimal wavelengths at which to describe concentrations of interferents. However significant changes in the spectrum brought about by lipemia, influence the outcome of calculations for haemoglobin or for bilirubin, or biliverdin, or blood substitutes and consequently it is necessary to select additional wavelengths to compensate for these interactions. Nevertheless, this is not a preferred approach.

Another method which may be employed is to use all of the absorbance spectrum, and perform either a principal component analysis or partial least squares analysis and effectively determine from the components that are optimised, the concentration of these different elements. However, a disadvantage of using either of these methods is that they are computationally intensive and consequently take more time to calculate and increase the length of time required to assess each sample.

A preferred method is to calculate the first derivative of certain portions of the absorbance spectra in respect of the particular interferent being measured. It is also possible to calculate the second, or third derivatives of absorbance, and such calculations are within the scope of this invention. However, each step of taking differences to calculate those derivatives is more time consuming and introduces more noise.

Smoothing of the absorbence data may be performed if necessary before processing the data.

In practice, an optimal combination of first derivatives of at least two portions of an absorbance spectrum generated from a scan of a plasma specimen containing a particular interferent, is used to calculate interferent concentration. The precise approach used depends on the interferent being measured.

There are three parts to the present invention. The first part of the present invention is to measure the amount of the blood substitute present in the serum/plasma specimen. In respect of Hemosol CLHb optimal results may be obtained by calculating the first derivative of absorbance measurements at wavelengths of approximately 541 nm, 558 nm, 600 nm and 616 nm.

The calibration equations outlined below cover the broad range of variability anticipated for the interferents. If low-end accuracy becomes a concern, separate calibrations can be developed: one for the high end, and a second, if the result predicted by the previous calibration is less than a predetermined level.

In order to calibrate the spectrophotometer for CLHb, serum specimens with normal appearance were spiked with 0 to 16.6 g/L CLHb, 0 to 3.2 g/L Hb, 0 to 4.0 g/L IL, 0 to 48.4 mg/dL BR and 0 to 4.0 mg/dL BV as shown in Table 1. No significant intercorrelation among the analytes was allowed. The specimens were run once immediately after preparation, and then repeated using different polypropylene pipette disposable tips. The Hb was prepared by replacing the normal plasma (by appearance) with water and lysing the erythrocytes through three freeze-thaw cycles. The Hb content of the supernatant of the lysate was measured on an Abbott Cell Dyn.™ The spectra were stored on diskettes. The analyses on a sample sets were performed by a statistical computer program and an algorithm was developed for CLHb. An independent sample sets were set aside for validation (referred to in the graphical representations as prediction) of the calibration equation, and is shown in Table 2.

TABLE 1

| Sample # | Actual Hemolink (g/L) | Hb (g/L) | IL (g/L) | BV (mg/dL) | BR (mg/dL) | Fitted Hemolink (g/L) |
|---|---|---|---|---|---|---|
| 1 | 4.91 | 0 | 0 | 0 | 0 | 4.95 |
| 2 | 4.91 | 0 | 0 | 0 | 0 | 5.00 |
| 3 | 2.62 | 0 | 0 | 0 | 0 | 2.86 |
| 4 | 2.62 | 0 | 0 | 0 | 0 | 2.88 |
| 5 | 0 | 0 | 0 | 0 | 0 | 0.19 |
| 6 | 0 | 0 | 0 | 0 | 0 | 0.10 |

TABLE 1-continued

| Sample # | Actual Hemolink (g/L) | Hb (g/L) | IL (g/L) | BV (mg/dL) | BR (mg/dL) | Fitted Hemolink (g/L) |
|---|---|---|---|---|---|---|
| 7 | 7.43 | 0 | 0 | 0 | 0 | 6.63 |
| 8 | 7.43 | 0 | 0 | 0 | 0 | 6.62 |
| 9 | 1.33 | 0 | 0 | 0 | 0 | 1.17 |
| 10 | 1.33 | 0 | 0 | 0 | 0 | 1.09 |
| 11 | 5.89 | 0 | 0 | 0 | 0 | 5.42 |
| 12 | 5.89 | 0 | 0 | 0 | 0 | 5.39 |
| 13 | 4.17 | 2.36 | 0 | 0 | 0 | 4.51 |
| 14 | 4.17 | 2.36 | 0 | 0 | 0 | 4.52 |
| 15 | 7.36 | 0.77 | 0 | 0 | 0 | 6.36 |
| 16 | 7.36 | 0.77 | 0 | 0 | 0 | 6.54 |
| 17 | 6.58 | 1.16 | 0 | 0 | 0 | 6.06 |
| 18 | 6.58 | 1.16 | 0 | 0 | 0 | 6.06 |
| 19 | 4.21 | 1.59 | 0 | 0 | 0 | 4.51 |
| 20 | 4.21 | 1.59 | 0 | 0 | 0 | 4.41 |
| 21 | 1.72 | 2.03 | 0 | 0 | 0 | 1.93 |
| 22 | 1.72 | 2.03 | 0 | 0 | 0 | 1.92 |
| 23 | 3.33 | 3.15 | 0 | 0 | 0 | 3.99 |
| 24 | 3.33 | 3.15 | 0 | 0 | 0 | 3.92 |
| 25 | 3.3 | 0 | 2.29 | 0 | 0 | 2.83 |
| 26 | 3.3 | 0 | 2.29 | 0 | 0 | 2.71 |
| 27 | 14.75 | 0 | 1.39 | 0 | 0 | 14.90 |
| 28 | 5.81 | 0 | 2.74 | 0 | 48.39 | 6.01 |
| 29 | 5.81 | 0 | 2.74 | 0 | 48.39 | 5.95 |
| 30 | 11.25 | 0 | 3.98 | 0 | 23.44 | 11.05 |
| 31 | 11.25 | 0 | 3.98 | 0 | 23.44 | 10.86 |
| 32 | 8.37 | 0 | 1.98 | 1.55 | 38.76 | 8.46 |
| 33 | 8.37 | 0 | 1.98 | 1.55 | 38.76 | 8.52 |
| 34 | 4.5 | 0 | 2.83 | 0.83 | 33.33 | 5.05 |
| 35 | 4.5 | 0 | 2.83 | 0.83 | 33.33 | 4.91 |
| 36 | 16.62 | 0 | 0 | 1.54 | 7.69 | 16.34 |
| 37 | 16.62 | 0 | 0 | 1.54 | 7.69 | 16.53 |
| 38 | 12.66 | 0 | 0 | 2.34 | 15.63 | 12.79 |
| 39 | 12.66 | 0 | 0 | 2.34 | 15.63 | 12.95 |
| 40 | 7.63 | 0 | 0 | 3.39 | 0 | 8.31 |
| 41 | 7.63 | 0 | 0 | 3.39 | 0 | 8.17 |
| 42 | 10.16 | 0 | 0 | 4.03 | 0 | 9.73 |
| 43 | 10.16 | 0 | 0 | 4.03 | 0 | 9.52 |
| 44 | 9.03 | 0 | 1.84 | 0 | 0 | 9.58 |
| 45 | 10.28 | 0 | 2.07 | 0 | 24.19 | 11.34 |
| 46 | 8.53 | 0 | 3.36 | 0 | 35.91 | 8.5 |
| 47 | 9.81 | 0 | 2.98 | 0.78 | 31.1 | 10.39 |
| 48 | 6.44 | 0 | 2.41 | 1.19 | 36.05 | 5.93 |
| 49 | 1.75 | 0 | 0 | 0 | 0 | 1.86 |
| 50 | 1.75 | 0 | 0 | 0 | 0 | 1.84 |

TABLE 2

| Sample # | Actual Hemolink (g/L) | Hb (g/L) | IL (g/L) | BV (mg/dL) | BR (mg/dL) | Predicted Hemolink (g/L) |
|---|---|---|---|---|---|---|
| 1 | 0.85 | 0 | 0 | 0 | 0 | 1.03 |
| 2 | 0.85 | 0 | 0 | 0 | 0 | 1.03 |
| 3 | 3.41 | 0 | 0 | 0 | 0 | 3.73 |
| 4 | 3.41 | 0 | 0 | 0 | 0 | 3.56 |
| 5 | 6.52 | 0 | 0 | 0 | 0 | 5.92 |
| 6 | 6.52 | 0 | 0 | 0 | 0 | 5.89 |
| 7 | 0.87 | 2.05 | 0 | 0 | 0 | 1.09 |
| 8 | 0.87 | 2.05 | 0 | 0 | 0 | 1.13 |
| 9 | 5.83 | 0.79 | 0 | 0 | 0 | 5.54 |
| 10 | 5.83 | 0.79 | 0 | 0 | 0 | 5.45 |
| 11 | 2.5 | 3.94 | 0 | 0 | 0 | 3.77 |
| 12 | 2.5 | 3.94 | 0 | 0 | 0 | 3.50 |
| 13 | 1.31 | 1.24 | 0 | 0 | 0 | 1.28 |
| 14 | 1.31 | 1.24 | 0 | 0 | 0 | 1.34 |
| 15 | 14.75 | 0 | 1.39 | 0 | 0 | 15.24 |
| 16 | 10.56 | 0 | 1.42 | 1.19 | 20.51 | 11.36 |
| 17 | 14.64 | 0 | 0 | 1.94 | 11.66 | 16.36 |
| 18 | 10.14 | 0 | 0 | 2.87 | 7.81 | 10.50 |
| 19 | 8.89 | 0 | 0 | 3.71 | 0 | 8.42 |
| 20 | 6.73 | 0 | 1.15 | 2.02 | 0 | 5.85 |
| 21 | 1.65 | 0 | 1.15 | 0 | 0 | 0.59 |

TABLE 2-continued

| Sample # | Actual Hemolink (g/L) | Hb (g/L) | IL (g/L) | BV (mg/dL) | BR (mg/dL) | Predicted Hemolink (g/L) |
|---|---|---|---|---|---|---|
| 22 | 7.38 | 0 | 0.7 | 0 | 0 | 7.02 |
| 23 | 2.9 | 0 | 1.37 | 0 | 24.19 | 2.67 |
| 24 | 5.63 | 0 | 1.99 | 0 | 11.72 | 4.51 |
| 25 | 4.19 | 0 | 0.99 | 0.78 | 19.38 | 4.04 |
| 26 | 2.25 | 0 | 1.42 | 0.42 | 16.67 | 1.94 |
| 27 | 8.31 | 0 | 0 | 0.77 | 3.85 | 7.78 |
| 28 | 6.33 | 0 | 0 | 1.17 | 7.81 | 6.23 |
| 29 | 3.81 | 0 | 0 | 1.69 | 0 | 3.58 |
| 30 | 5.08 | 0 | 0 | 2.02 | 0 | 4.72 |

Figure 1:
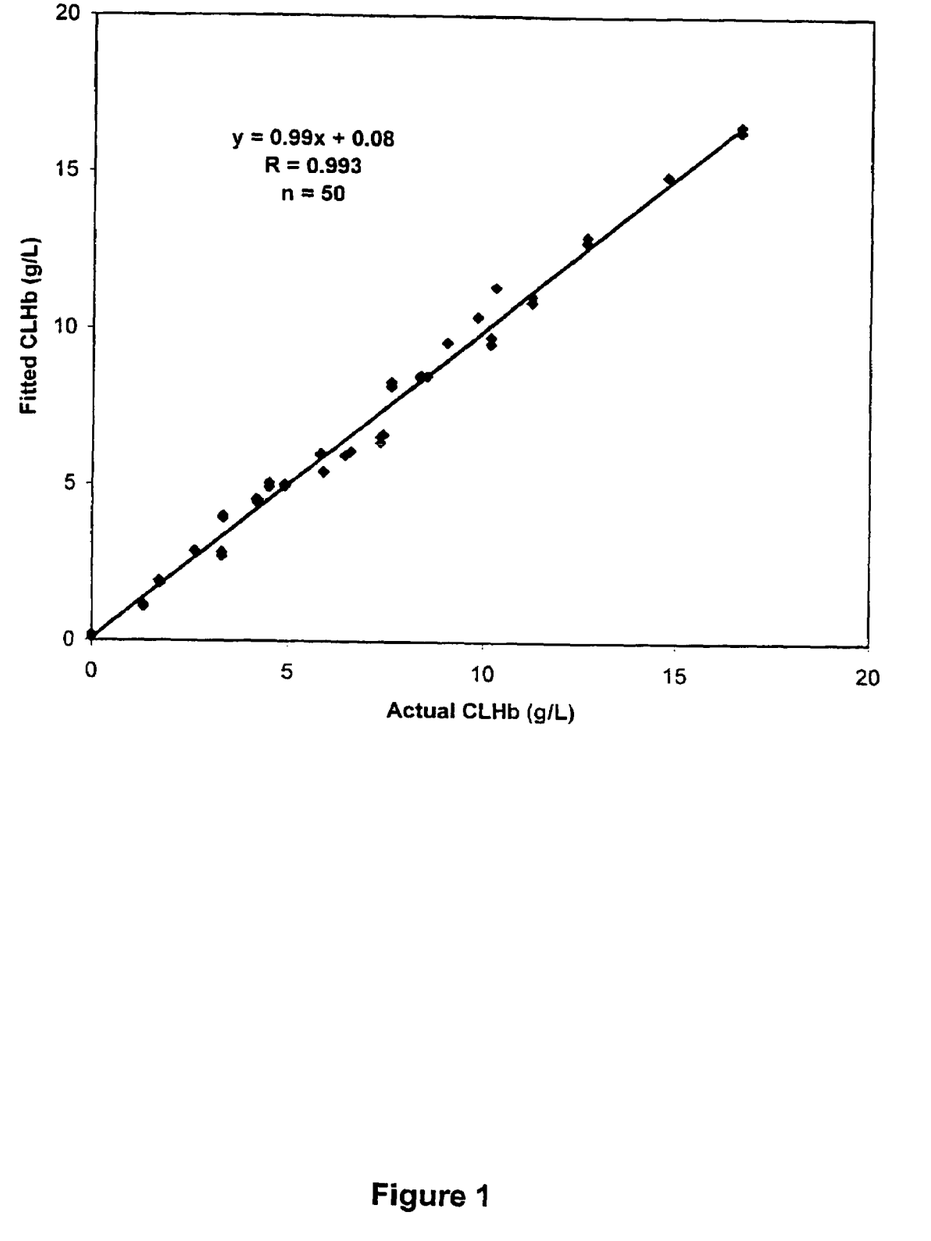
FIG. 1 is a graphic representation of a linear regression fit of the data generated from the CLHb calibration.

FIG. 1 is a graphic representation of a linear regression fit of the data generated from the CLHb calibration. The algorithm which was developed for Hb based on this data is as follows:

$$\text{g/L CLHb} = 23.97(541\text{ nm}) - 76.01(558\text{ nm}) + 130.84(600\text{ nm}) - 113.61(616\text{ nm}) + 0.30$$

where (Xnm) is the first derivative of the absorbance measured at the wavelength specified.

Figure 2:
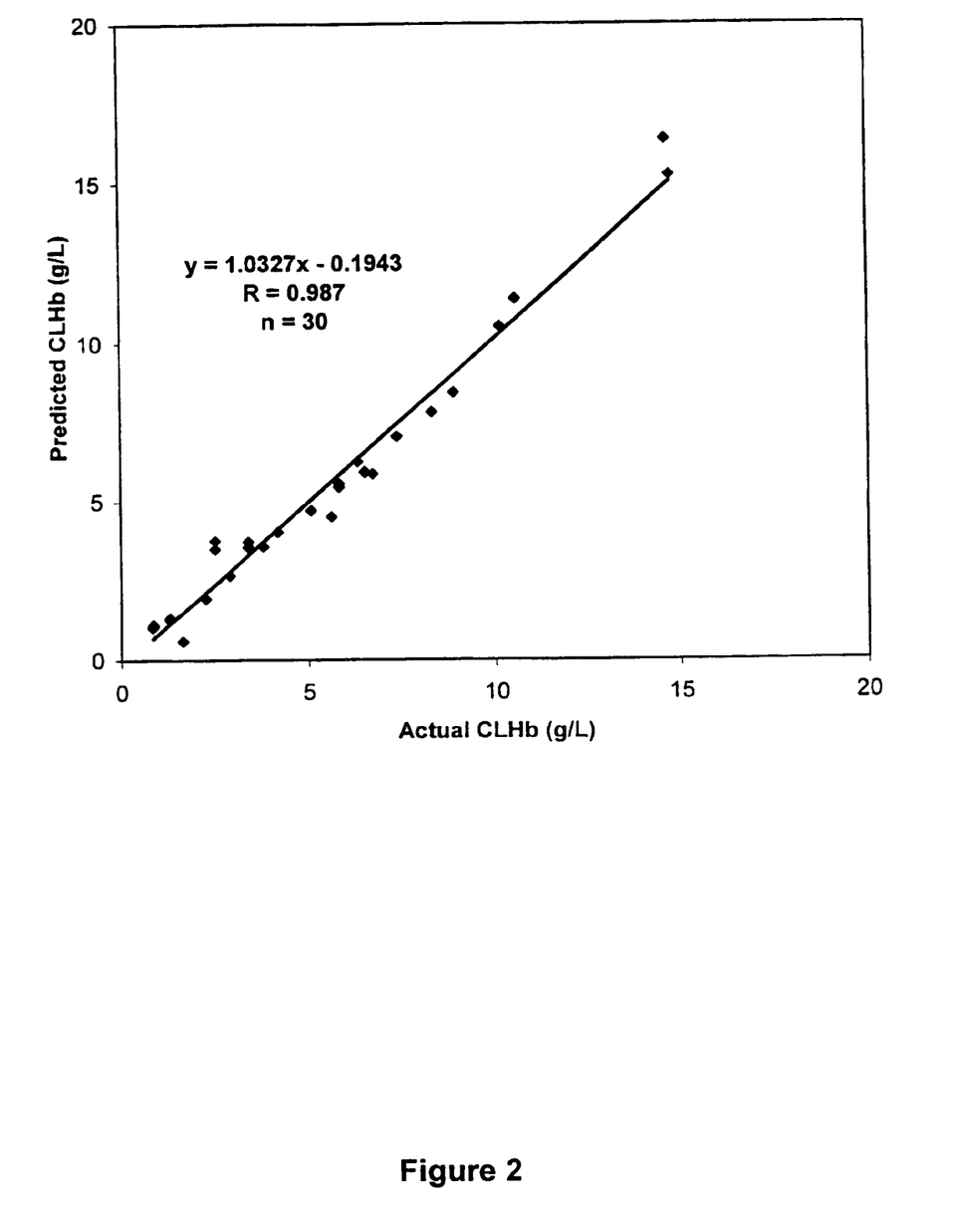
FIG. 2 provides a graphic representation of the results of linear regression fit for predicted CLHb concentration, for samples not used in the calibration processes.

FIG. 2 provides a graphic representation of the results of linear regression fit for predicted CLHb concentration, for samples not used in the calibration processes.

Figure 3:
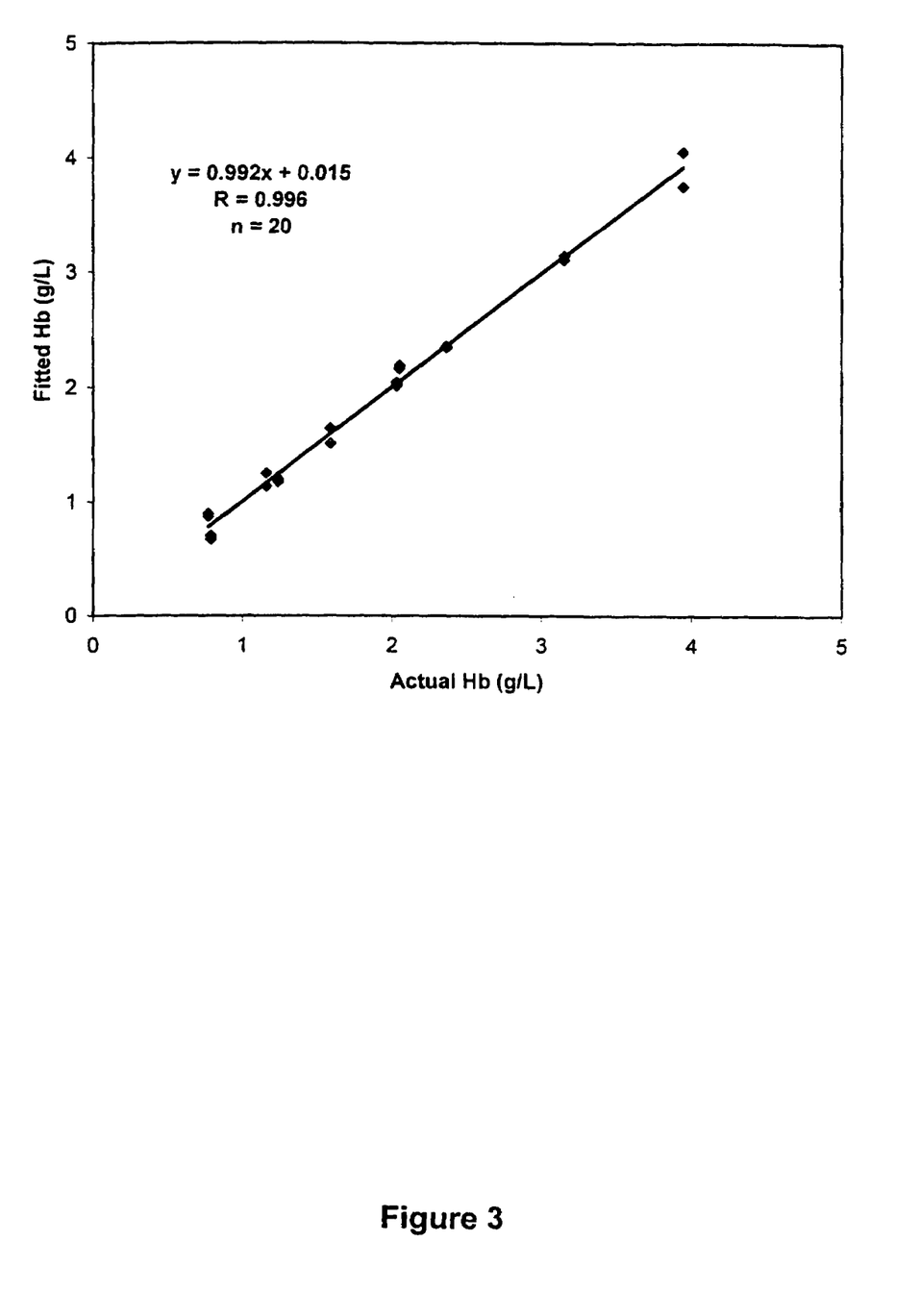
FIG. 3 provides a representation of the results of a linear regression fit of data generated from true Hb calibration in the presence of cross-linked Hb and other interferents (IL, BR, BV).

FIG. 3 provides a graphic representation of the results of a linear regression fit of the data generated from the true Hb calibration with the presence of cross-linked Hb and other interferents (IL, BR, BV). Table 3 provides the individual data points obtained when performing this calibration. The algorithm which was developed as a result of this calibration is as follows:

$$\text{g/L Hb} = -0.72 + 30.72(558) - 17.40(570) + 171.14(730)$$

where numbers in the parenthesis are the first derivative of the absorbance at the wavelengths (nm) shown.

The second part of the present invention is to quantify the relationship between measured amounts of each analyte with respect to the amount of blood substitute present in the serum or plasma specimen, for a particular blood analyzer; these equations which allow one to extrapolate the analyte concentration at zero g/L blood substitute must be validated at different levels of the analyte, and if the slopes of the regression lines for different analyte concentration vary with analyte concentration, an average slope value may be used. In this specification, analyte refers to substances routinely measured on a blood analyzer. Tables 4 and 5 give the measured concentrations (all in S. I. units) of various analytes on two different analyzers, in the presence of different levels of CLHb. The analytes which are severely affected by the CLHb are shown in shaded sections of Table 5.

Figure 4:
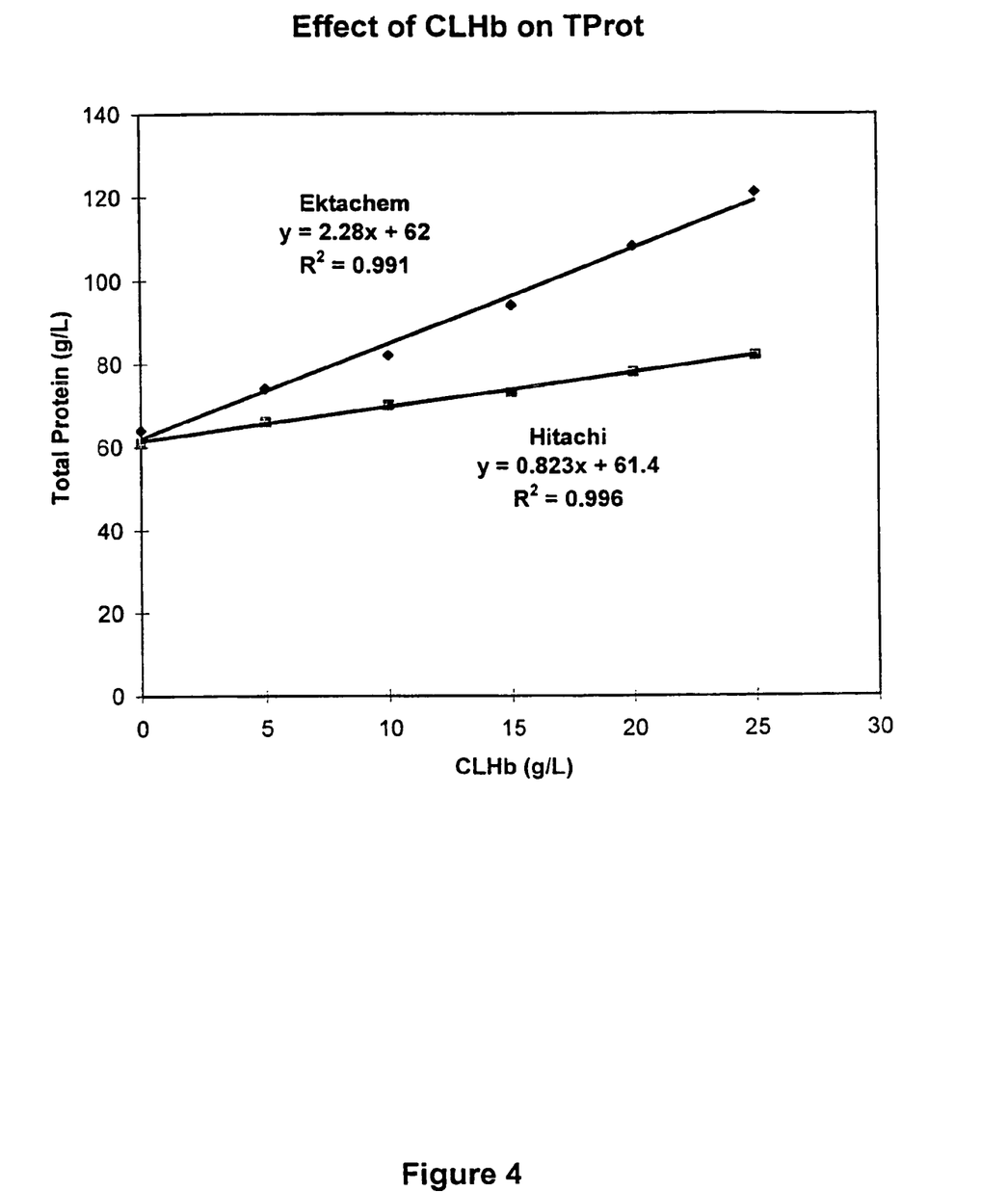
FIG. 4 is a graphical representation of a linear regression fit for data in respect of total protein.
Figure 5:
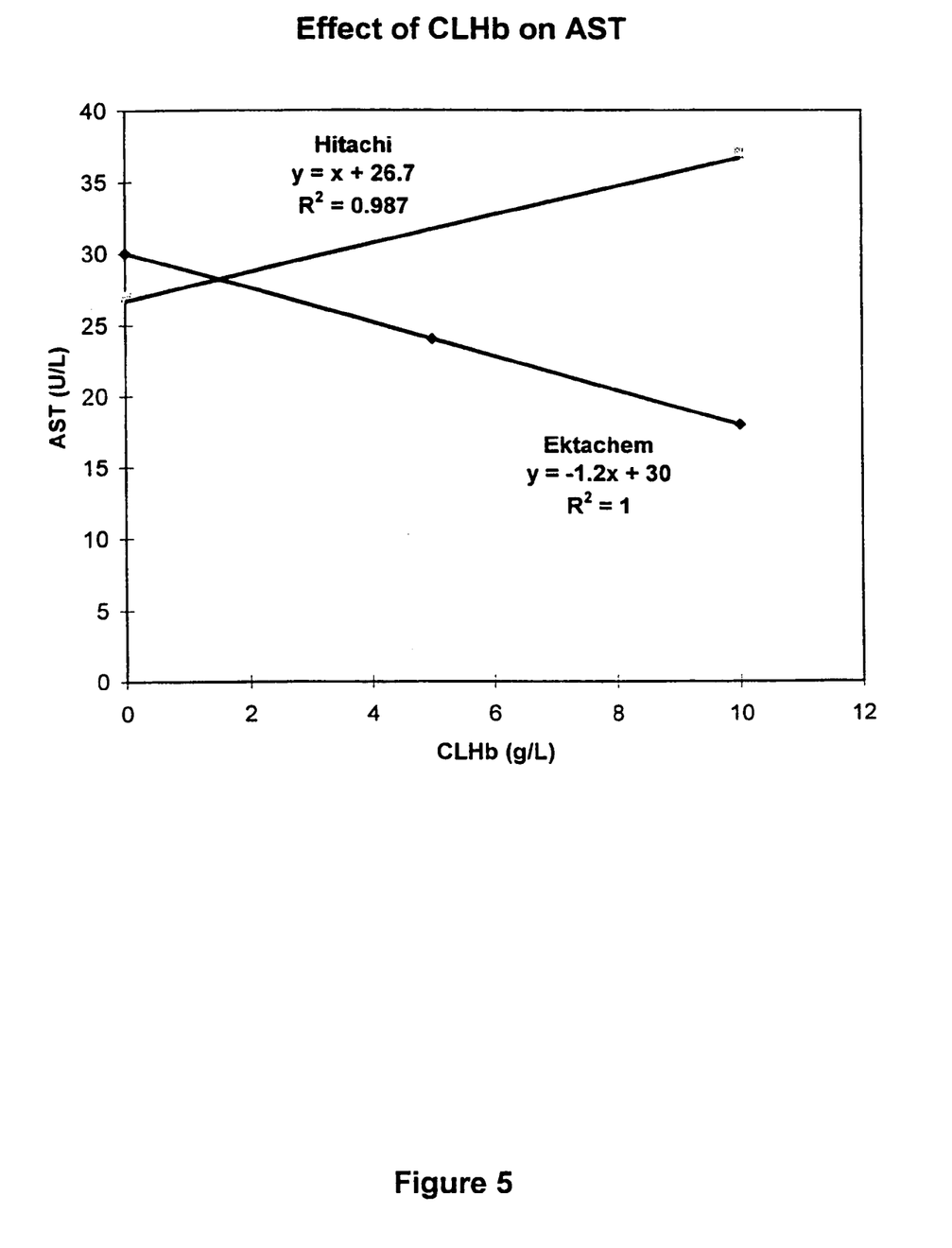
FIG. 5 is a graphical representation of linear regression fit for data in respect of aspartate aminotransferase.
Figure 6:
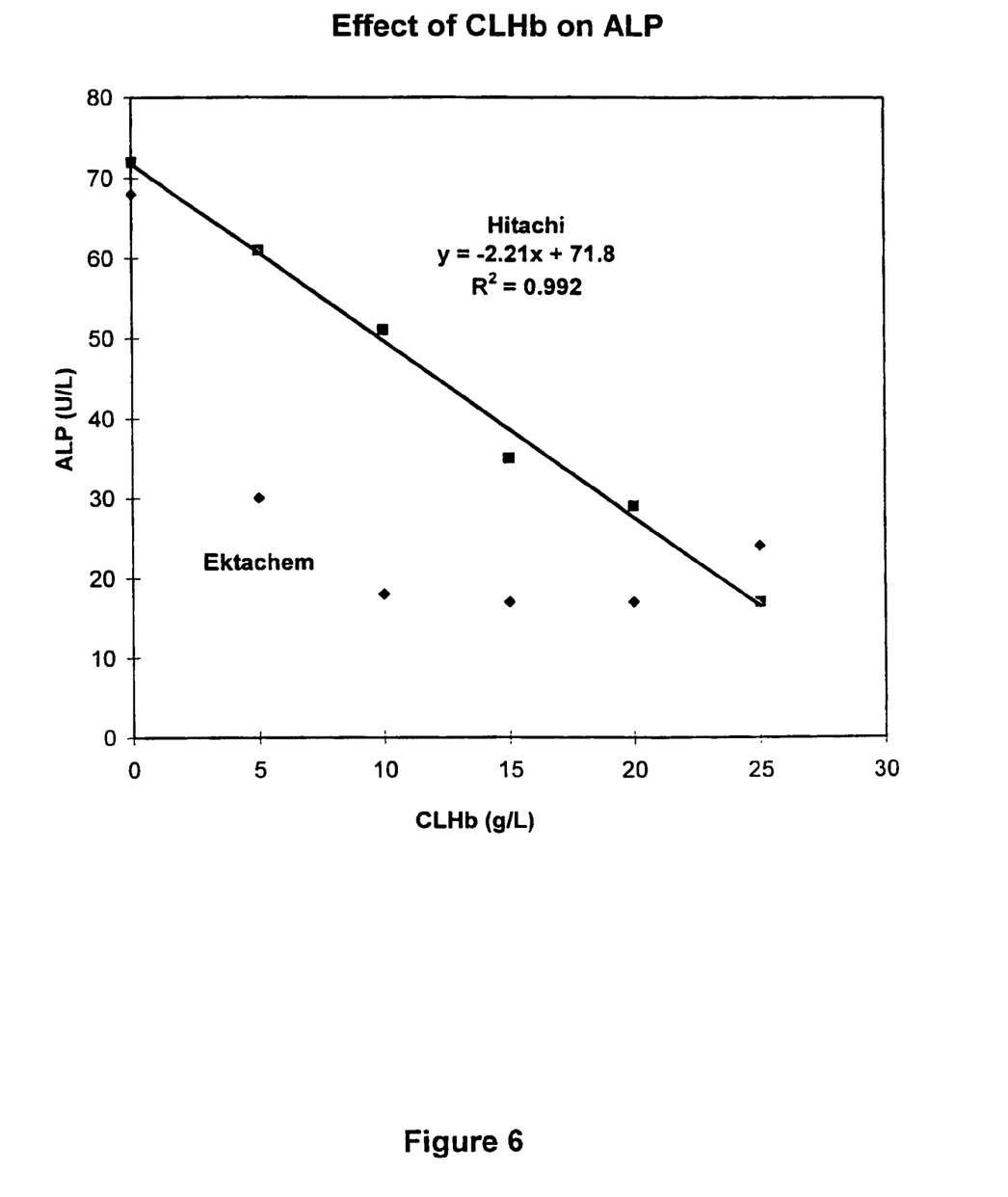
FIG. 6 is a graphical representation of linear regression fit for data in respect of alkaline phosphatase.
Figure 7:
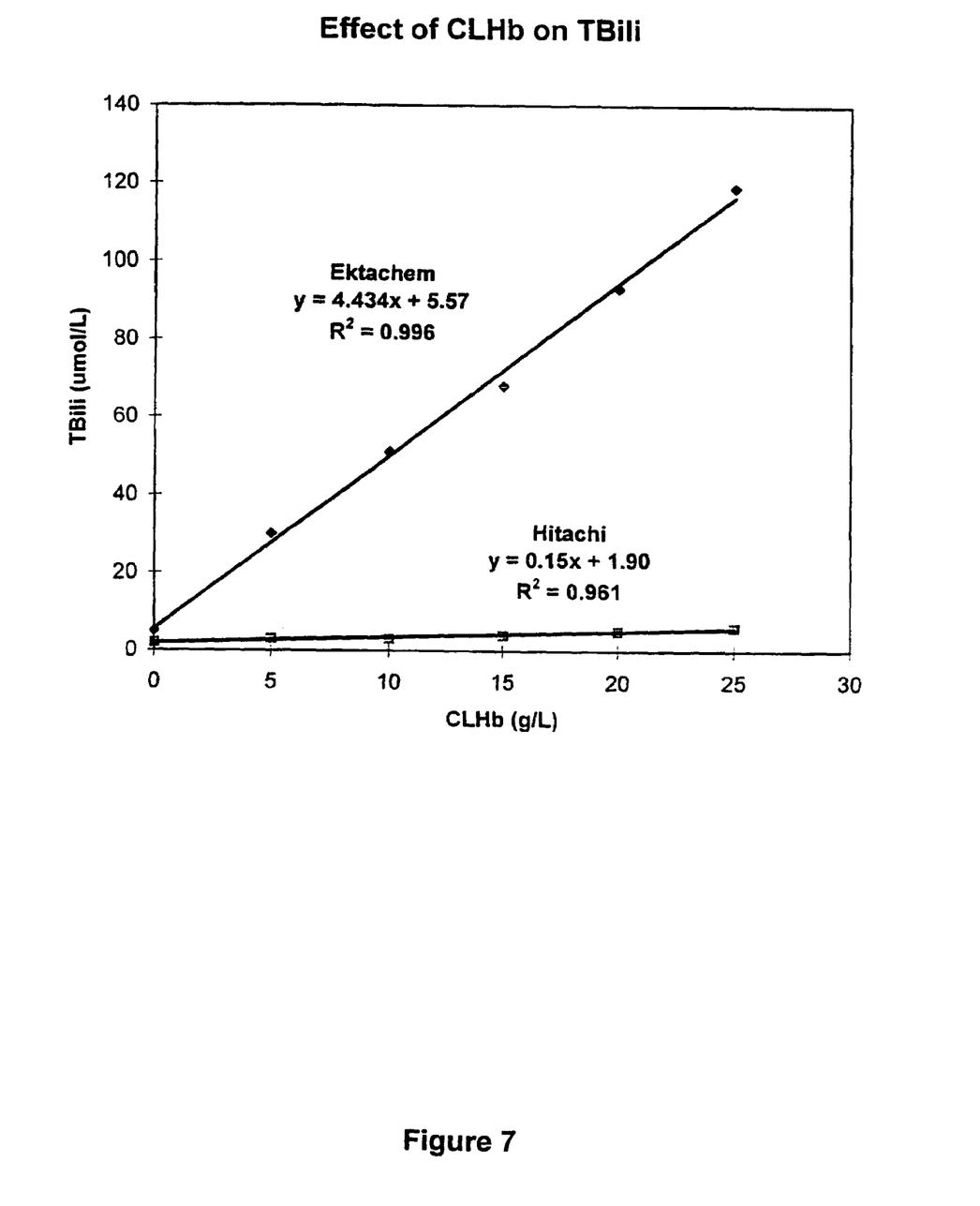
FIG. 7 is a graphical representation of linear regression fit for data in respect of total bilirubin.

FIGS. 4 to 7 are graphical representations of linear regression fits, where appropriate, for the measured analytes in response to different amounts of added CLHb. FIG. 4 is for total protein (Tprot) when measured on the Kodak Ektachem and the Hitachi 717; FIG. 5 is for aspartate aminotransferase (AST) when measured on the Kodak Ektachem and the Hitachi 717; FIG. 6 is for alkaline phosphatase (ALP) when measured on the Kodak Ektachem and the Hitachi 717; and FIG. 7 is for total bilirubin (Tbili) when measured on the Kodak Ektachem and the Hitachi 717. Where appropriate, the linear regression equations are shown next to the corresponding regression line. To illustrate how this invention works, let us use serum total protein measurement on the Kodak Ektachem as the test which is affected by the presence of CLHb in a patient's serum:

From FIG. 4, $y = 2.28x + c$, where $y = $ g/L total protein (in presence of CLHb)

$x = $ g/L CLHb present

TABLE 3

| CLHb (g/L) | Actual Hb (g/L) | Fitted Hb (g/L) |
|---|---|---|
| 4.17 | 2.36 | 2.35 |
| 4.17 | 2.36 | 2.34 |
| 7.36 | 0.77 | 0.89 |
| 7.36 | 0.77 | 0.87 |
| 6.58 | 1.16 | 1.25 |
| 6.58 | 1.16 | 1.13 |
| 4.21 | 1.59 | 1.51 |
| 4.21 | 1.59 | 1.64 |
| 0.87 | 2.05 | 2.18 |
| 0.87 | 2.05 | 2.16 |
| 5.83 | 0.79 | 0.67 |
| 5.83 | 0.79 | 0.70 |
| 2.50 | 3.94 | 3.76 |
| 2.50 | 3.94 | 4.05 |
| 1.31 | 1.24 | 1.19 |
| 1.31 | 1.24 | 1.17 |
| 1.72 | 2.03 | 2.01 |
| 1.72 | 2.03 | 2.04 |
| 3.33 | 3.15 | 3.11 |
| 3.33 | 3.15 | 3.15 |

TABLE 4

| CLHb (g/L) | Na | K | Cl | HCO3 | Ca | Mg | Creat | Urea |
|---|---|---|---|---|---|---|---|---|
| KODAK EKTACHEM | | | | | | | | |
| 0 | 138 | 4.3 | 104 | 16 | 2.38 | 0.65 | 73 | 3.9 |
| 5 | 137 | 4.2 | 104 | 16 | 2.40 | 0.64 | 70 | 3.9 |
| 10 | 137 | 4.3 | 104 | 16 | 2.42 | 0.63 | 68 | 3.9 |
| 15 | 137 | 4.2 | 103 | 15 | 2.40 | 0.62 | 67 | 3.9 |
| 20 | 137 | 4.3 | 103 | 15 | 2.40 | 0.62 | 66 | 3.9 |
| 25 | 136 | 4.2 | 103 | 15 | 2.41 | 0.61 | 66 | 3.9 |
| HITACHI 717 | | | | | | | | |
| 0 | 140 | 4.3 | 105 | 12 | 2.09 | 0.72 | 86 | 4.4 |
| 5 | 142 | 4.3 | 105 | 13 | 2.13 | 0.75 | 81 | 4.5 |
| 10 | 140 | 4.2 | 104 | 14 | 2.10 | 0.80 | 81 | 4.4 |
| 15 | 139 | 4.2 | 103 | 14 | 2.10 | 0.82 | 82 | 4.4 |
| 20 | 138 | 4.2 | 102 | 14 | 2.08 | 0.83 | 82 | 4.5 |
| 25 | 137 | 4.2 | 101 | 14 | 2.09 | 0.86 | 84 | 4.3 |

TABLE 5

| CLHb (g/L) | Glu | TProt | AST | GGT | LDH | CK | ALP | TBili |
|---|---|---|---|---|---|---|---|---|
| KODAK EKTACHEM | | | | | | | | |
| 0 | 4.6 | 64 | 30 | 45 | 112 | 394 | 68 | 5 |
| 5 | 4.7 | 74 | 24 | 104 | 236 | 404 | 30 | 30 |
| 10 | 5.0 | 82 | 18 | 133 | 219 | 388 | 18 | 51 |
| 15 | 5.2 | 94 | 15 | 78 | 244 | 396 | 17 | 68 |
| 20 | 5.4 | 108 | 13 | 65 | 196 | 388 | 17 | 93 |
| 25 | 5.5 | 121 | | 144 | | | 24 | 119 |
| HITACHI 717 | | | | | | | | |
| 0 | 4.5 | 61 | 27 | 39 | 100 | 283 | 72 | 2 |
| 5 | 4.9 | 66 | 31 | 36 | 95 | 296 | 61 | 3 |
| 10 | 5.2 | 70 | 37 | 37 | 100 | 299 | 51 | 3 |
| 15 | 5.5 | 73 | 37 | 40 | 100 | 288 | 35 | 4 |
| 20 | 5.7 | 78 | 32 | 40 | 106 | 306 | 29 | 5 |
| 25 | 6.1 | 82 | 33 | 42 | 106 | 316 | 17 | 6 |

$c = $ g/L total protein (in presence of zero CLHb)

In this example, c=62 g/L

The third part of the present invention is combining the first two parts of the invention so as to extrapolate the concentration of the analyte to give an analyte concentration when there is no blood substitute present. For illustrative purposes, let us say that the measured amount of CLHb in the serum specimen is 20 g/L and the measured amount of total protein in the same specimen is 108 g/L.

| | |
|---|---|
| Question: | What is the actual serum total protein? |
| Answer: | From the apparent or measured total protein concentration (in this case it is 108 g/L), subtract the measured g/L CLHb times the slope of the regression line (in this case it is 2.28), from the measured value |
| | The answer is 62.4 g/L. |

This is in good agreement with the known value of 62 g/L. The accuracy of this correction will depend on the accuracy of measurement of the blood substitute, and the reliability of the slope used.

As part of this invention, it is also understood that other interferents can be measured accurately in the presence of blood substitutes. This may be necessary to determine if other interferents are present in sufficient quantities that will invalidate correction for blood substitutes. As will be readily understood by those skilled in the art, several algorithms can be developed for each interferent using different groups of wavelengths with the resultant prediction performance by the different algorithms for the same interferent being similar. Also, algorithms can be developed for any interferent or combinations of interferents including blood substitutes, which will enable one to adjust measured analyte concentrations, for the presence of one or more interferents.

While the invention has been particularly shown and described with reference to certain embodiments, it will be understood by those skilled in the art that various other changes in form and detail may be made without departing from the scope of the invention.

We claim:

1. A method of determining a corrected concentration of an analyte contained in a specimen comprising a blood substitute interferent and a non-blood substitute interferent, said method comprising the steps of:
   i) providing a first calibration algorithm for said blood substitute interferent, a second calibration algorithm for said non-blood substitute interferent, a first linear equation defining a relationship between a measured concentration of said analyte and a concentration of said blood substitute interferent, and a second linear equation defining a relationship between a measured concentration of said analyte and a concentration of said non-blood substitute interferent, said first and second calibration algorithms developed using a calibration set comprising variable amounts of said blood substitute interferent and said non-blood substitute interferent;
   ii) measuring an absorbance or reflectance of radiation of said specimen in a tube or a pipette tip, wherein said measuring is performed in the absence of any reaction step that generates a chromophore within said specimen;
   iii) using said first and second calibration algorithms and said absorbance or reflectance measured in step (ii) to calculate a concentration of said blood substitute interferent and a concentration of said non-blood substitute interferent in said specimen; followed by
   iv) determining an initial concentration of said analyte in said specimen disposed within an analysis slide with a slide analyzer, and
   v) using said first and second linear equations from step (i), said concentrations from step (iii), and said initial concentration from step (iv), to determine said corrected concentration of said analyte.

2. The method of claim 1, wherein said analyte is selected from the group consisting of Na, K, Cl, $HCO_3$, Ca, Mg, creatinine, urea, total protein, gamma glutamyl transferase (GGT), aspartate amino transferase (AST), lactate dehydrogenase (LDH), creatine kinase (CK), alkaline phosphatase (ALP) and total bilirubin (Tbili).

3. The method of claim 1 wherein reflectance is used in step (ii).

4. The method of claim 1 wherein the radiation is in the range of 474–910 nm.

5. The method of claim 1 wherein absorbance is used in step (ii).

6. The method of claim 1, wherein said non-blood substitute interferent is selected from the group consisting of haemoglobin (Hb), bilirubin (BR), biliverdin (BV), turbidity and a mixture thereof.

7. The method of claim 1, wherein said blood substitute interferent is cross-linked hemoglobin.

8. A method of determining a corrected concentration of an analyte contained in a specimen comprising a blood substitute interferent, said method comprising the steps of:
   i) providing a calibration algorithm for said blood substitute interferent and a linear equation defining a relationship between a measured concentration of said analyte and a concentration of said blood substitute interferent, said calibration algorithm developed using a calibration set comprising variable amounts of said blood substitute interferent;
   ii) measuring an absorbance or reflectance of radiation of said specimen in a tube or a pipette tip, wherein said measuring is performed in the absence of any reaction step that generates a chromophore within said specimen;
   iii) using said calibration algorithm and said absorbance or reflectance measured in step (ii) to calculate a concentration of said blood substitute interferent; followed by
   iv) determining an initial concentration of said analyte in said specimen disposed within an analysis slide with a slide analyzer, and
   v) using said linear equation from step (i), said concentration from step (iii), and said initial concentration from step (iv), to determine said corrected concentration of said analyte.

9. The method of claim 8, wherein said analyte is selected from the group consisting of Na, K, Cl, $HCO_3$, Ca, Mg, creatinine, urea, total protein, gamma glutamyl transferase (GGT), aspartate amino transferase (AST), lactate dehydrogenase (LDH), creatine kinase (CK), alkaline phosphatase (ALP) and total bilirubin (Tbili).

10. The method of claim 8, wherein reflectance is used in step (ii).

11. The method of claim 8, wherein the radiation is in the range of 474–910 nm.

12. The method of claim 8, wherein absorbance is used in step (ii).

13. The method of claim 8, wherein said blood substitute interferent is cross-linked hemoglobin.

* * * * *